(12) United States Patent
Brody

(10) Patent No.: US 6,965,794 B2
(45) Date of Patent: Nov. 15, 2005

(54) APPARATUS FOR ROUTING ELECTROMYOGRAPHY SIGNALS

(75) Inventor: Lee Richard Brody, Somerville, MA (US)

(73) Assignee: Fasstech, Inc., North Billerica, MA (US)

(*) Notice: Subject to any disclaimer, the term of this patent is extended or adjusted under 35 U.S.C. 154(b) by 424 days.

(21) Appl. No.: 10/119,979

(22) Filed: Apr. 10, 2002

(65) Prior Publication Data

US 2003/0069514 A1    Apr. 10, 2003

Related U.S. Application Data

(60) Provisional application No. 60/327,324, filed on Oct. 5, 2001.

(51) Int. Cl.[7] ............................................... A61B 5/04
(52) U.S. Cl. ........................................ 600/546; 600/393
(58) Field of Search ............................ 600/546, 393, 600/391

(56) References Cited

U.S. PATENT DOCUMENTS

| | | | |
|---|---|---|---|
| 5,096,669 A | * | 3/1992 | Lauks et al. ................. 600/573 |
| 5,483,967 A | * | 1/1996 | Ohtake ........................ 600/508 |
| 6,002,957 A | * | 12/1999 | Finneran ..................... 600/546 |
| 6,463,322 B1 | * | 10/2002 | Lutz et al. ................... 600/546 |
| 6,560,479 B2 | * | 5/2003 | van Drongelen ............ 600/544 |
| 2004/0054273 A1 | * | 3/2004 | Finneran et al. ............. 600/546 |

* cited by examiner

Primary Examiner—Eric F. Winakur
Assistant Examiner—Matthew J. Kremer
(74) Attorney, Agent, or Firm—Cesari and McKenna, LLP

(57) ABSTRACT

An EMG monitoring system includes a matrix of detection electrode arrays that is positioned on the patient along his or her spine. The arrays are electrically connected through a switching mechanism to EMG amplifiers that are included in conventional monitoring instrumentation. A switch controller operates the switches to provide signals to the EMG amplifiers from selected sets of detection electrode arrays. The controller controls the switches to provide signals simultaneously to each EMG amplifier. If the monitoring instrumentation includes four EMG amplifiers, the matrix of electrode arrays and the switching mechanism may be used to take simultaneous measurements at two different spinal levels. If additional EMG amplifiers are included, simultaneous measurements at additional spinal levels may also be made. The matrix may also include redundant arrays and/or electrodes, such that the clinician can select the sets of electrodes that conform to the size of the patient.

12 Claims, 4 Drawing Sheets

APPARATUS FOR ROUTING ELECTROMYOGRAPHY SIGNALS

CROSS-REFERENCE TO RELATED APPLICATIONS

The present application claims the benefit of U.S. Provisional Patent Application Ser. No. 60/327,324, which was filed on Oct. 5, 2001, by Lee Richard Brody for a APPARATUS FOR ROUTING ELECTROMYOGRAPHY SIGNALS and is hereby incorporated by reference.

BACKGROUND OF THE INVENTION

1. Field of the Invention

The invention relates generally to systems for monitoring electromyography signals.

2. Background Information

Electromyography (EMG) signals are bioelectric signals that are generated during muscle contraction, and the energy of the EMG signals is proportional to muscle tone. Chiropractors and other healthcare clinicians currently monitor surface EMG signals to evaluate paraspinal muscle tone. Each EMG signal is detected using a detection electrode array that is held on the skin above the muscle.

The known prior detection electrode arrays are hand-held devices that include two differential electrodes. A ground electrode may also be included in the array or, alternatively, the ground electrode may be attached separately to the patient's body. The differential electrodes are electrically connected to EMG amplifiers that are included in monitoring instrumentation. The EMG amplifiers operate in a known manner to amplify, filter, process and convert the EMG signals into signals that can be further processed, for example, by a personal computer. The EMG amplifiers, which manipulate signals that are in the 1 to 25 millionth of a volt range, are relatively complex, and thus, expensive. The monitoring instrumentation typically includes either two or four EMG amplifiers. Two amplifiers are required for the "mapping" of muscle tone along the spine, while other measurement protocols may utilize all four amplifiers.

A clinician performs the mapping protocol while the patient is in a particular stable posture, such as a seated neutral position. As appropriate, additional protocols may be performed with the patient in other postures. The mapping protocol involves taking surface EMG measurements from two muscle sites simultaneously, with the two arrays held respectively in position on either side of the spine at particular spinal levels. The two EMG measurements are taken at a given position after the signals stabilize at the EMG amplifiers. Thereafter, the clinician moves the two arrays to a next spinal level and records the EMG signals on either side of the spine, and so forth, until measurements are taken at typically between fifteen and twenty-five spinal levels.

The accuracy of the bi-lateral muscle tone measurements depends, in large part, on the skill of the clinician. First, the clinician must hold the arrays above the appropriate muscles and in the appropriate positions relative to the spine. Further, the clinician must place the arrays in place long enough for the signals to stabilize before the measurements are taken. Also, the clinician must make sure that the patient remains in a desired posture throughout the relatively time consuming process of repeatedly placing the arrays against the body, taking the measurements, and moving the arrays to a next location, and so forth. If the measurements must be repeated with additional postures, the clinician must accurately repeat the entire process. For patients with painful back or spinal conditions, the protocol may be inconvenient, if not impossible, to complete because the patient may not be able to remain in a desired posture throughout the time-consuming process.

SUMMARY OF THE INVENTION

An EMG monitoring system includes a matrix of detection electrode arrays that is positioned on the patient along his or her spine. The arrays are electrically connected through a switching mechanism to EMG amplifiers that are included in conventional monitoring instrumentation. A switch controller operates the switches to provide signals to the EMG amplifiers from selected sets of detection electrode arrays. Measurements can thus be taken along the entire spine without having to reposition the electrode arrays.

The controller controls the switches to provide signals simultaneously to each EMG amplifier. If the monitoring instrumentation includes four EMG amplifiers, the matrix of electrode arrays and the switching mechanism may be used to take simultaneous measurements at two different spinal levels. If additional EMG amplifiers are included, simultaneous measurements at additional spinal levels may also be made.

The matrix of arrays and the lines electrically connecting the arrays to the switching mechanism may be contained in two adhesive strips, such that the matrix remains in place, regardless of changes in posture. Alternatively, the matrix and connecting lines may be housed in a re-usable pad that is attached to the patient with a two-sided medical-grade adhesive sheet. The sheet has holes which are strategically located relative to the electrodes, to hold the electrodes in contact with the patient.

The matrix may include redundant arrays and/or electrodes, such that the clinician can select sets of electrodes that conform to the size of the patient. For example, the clinician may use adjacent arrays and adjacent electrodes within the respective arrays for the smallest patients. For somewhat larger patients, the clinician may use adjacent arrays and non-adjacent electrodes within the respective arrays, and so forth. Thus, the same matrix may be used for various sized patients.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
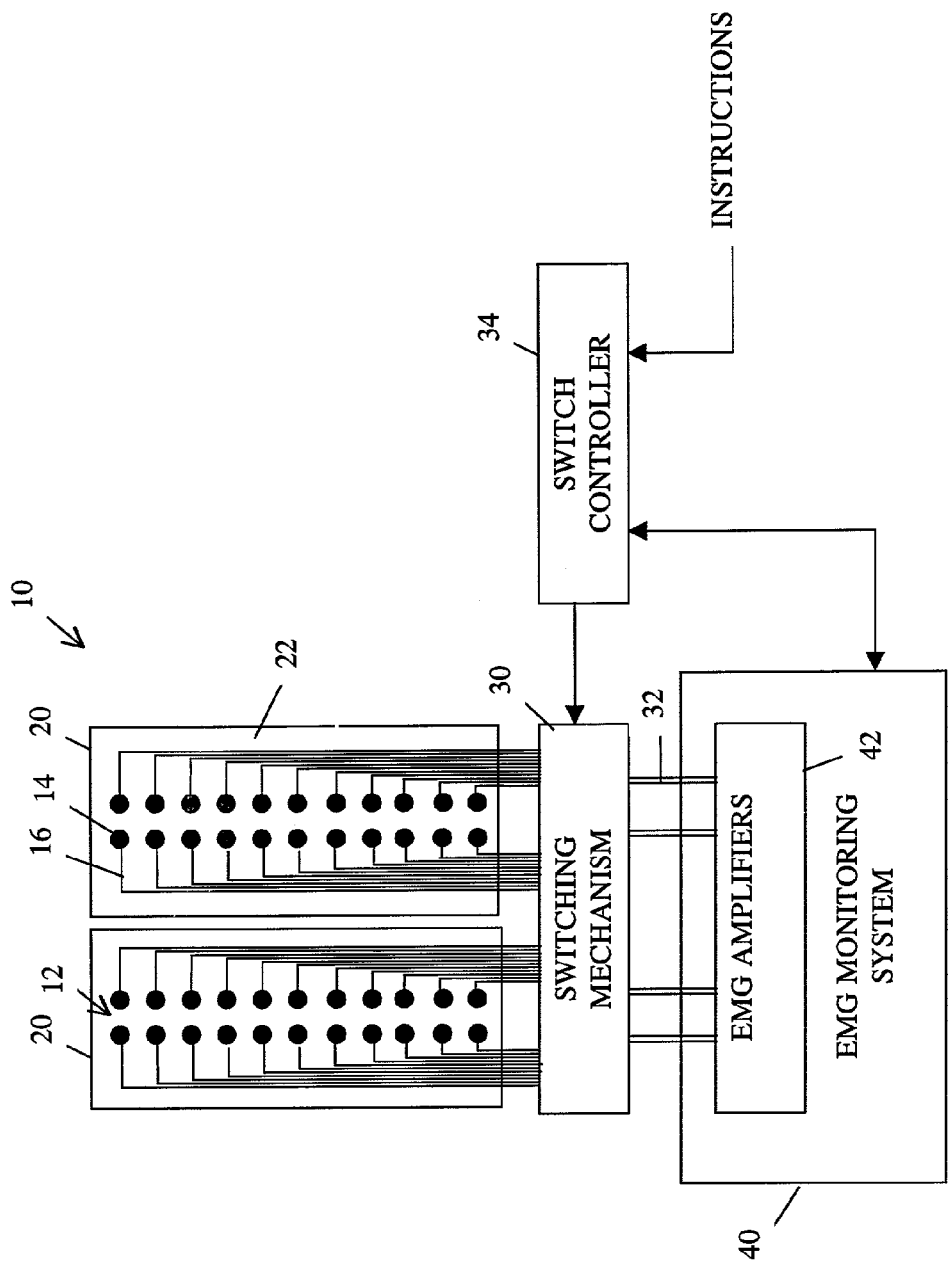
FIG. 1 illustrates a system that is constructed in accordance with the invention.

As depicted in FIG. 1, a matrix 10 includes a plurality of detection electrode arrays 12 that are spaced along two adhesive strips 20. The arrays 12 of electrodes 14 are arranged such that the individual electrodes 14 align with appropriate muscles when the strips are placed essentially vertically on either side of a patient's spine. A plurality of lines 16 electrically connect the electrodes 14 to a switching mechanism 30, which selectively provides the signals from the individual arrays 12 to EMG amplifiers 42 that are included in EMG monitoring instrumentation 40. In the system depicted in the drawing the monitoring instrumentation operates in a conventional manner and includes four EMG amplifiers. Accordingly, the signals from the arrays 12 are switched over four lines 32 to the respective amplifiers 42, such that measurements from two spinal levels can be made simultaneously. If additional EMG amplifiers are included in the EMG monitoring instrumentation, measurements from other spinal levels can be taken simultaneously by including an appropriate number of additional lines 32 and expanding the switching mechanism 30.

The switching mechanism 30, which may include individual switches, multiplexors, and so forth, operates under the control of a switch controller 34 and supplies the signals from selected arrays 12 to the EMG amplifiers 42. If, for example, the clinical protocol requires measurements to be taken along the entire spine, the switch controller 34 operates the switching mechanism 30 to pass the signals from the first array 12 in each strip 20, that is, from the arrays at the top of the spine, to one pair of the EMG amplifiers 42 and the signals from the second arrays 12 in each strip to the second pair of EMG amplifiers. The monitoring instrumentation 40 then takes measurements when the signals provided to the EMG amplifiers 42 stabilize. The switch controller 34 next controls the switching mechanism 30 to supply the signals from the next two arrays 12 in each strip to the EMG amplifiers 42, and so forth, until measurements from all of the arrays have been taken. The protocol measurements are thus taken relatively quickly, since the individual arrays do not have to be repositioned between measurements.

If the protocol requires that measurements are to be taken with another posture, the clinician instructs the patient to move to the new posture while the matrix 10 remains in place. The signals from the appropriate arrays 12 are then supplied to the monitoring instrumentation 40 in the same manner as discussed above. Alternatively, the protocol may require that only selected measurements be made in the new posture, and the switching mechanism 34 provides the signals from the appropriate arrays 12 to the instrumentation 40. The protocols can be performed as soon as the patient is settled in the new posture, since the matrix 10 remains in position on the patient's body as he or she moves to the new posture.

The switch controller 34 may be pre-programmed to perform the protocols. Alternatively, or in addition, the clinician may provide instructions for the different protocols or variations thereof. For example, the clinician may determine that the measurements taken along certain portions of the spine should be repeated, based on the results of earlier measurements. The clinician then provides the appropriate instructions to the switch controller 30, and the repeat measurements can be readily taken when the switches again supply the signals from the appropriate arrays 12 to the EMG amplifiers 42. Using prior systems, the clinician would instead have to reposition the arrays in each of the selected locations to take the additional measurements.

Aside from increasing the speed with which the various protocols can be performed, the matrix 10 ensures greater accuracy of the measurements. Using the matrix, the clinician places the arrays in the correct positions along the spine for the individual measurements. Further, the arrays remain in the same positions while measurements for different protocols or repeat measurements for the same protocol are taken, and the measurements can thus be reliably compared. This is in contrast to known prior systems in which handheld arrays are repositioned for each measurement, and may thus be inaccurately placed for some of the measurements, and/or placed in different relative positions for repeat measurements.

The strips 20 and the electrodes 14 included therein are disposable. The matrix 10 is sized differently for infants, children and adults. The vertical distances between the individual arrays in, for example, the infant-sized matrix, are relatively small while the vertical distances for the other sizes of matrix are proportionately larger. Further, the horizontal distances between the individual electrodes in the arrays are smaller for the infant-sized matrix. Within a given matrix, however, the vertical and horizontal distances between the individual arrays and the individual electrodes are constant. A ground electrode (not shown) may be included in one or both of the strips 20. Alternatively, the ground electrode may be attached separately to the patient's body.

Figure 2:
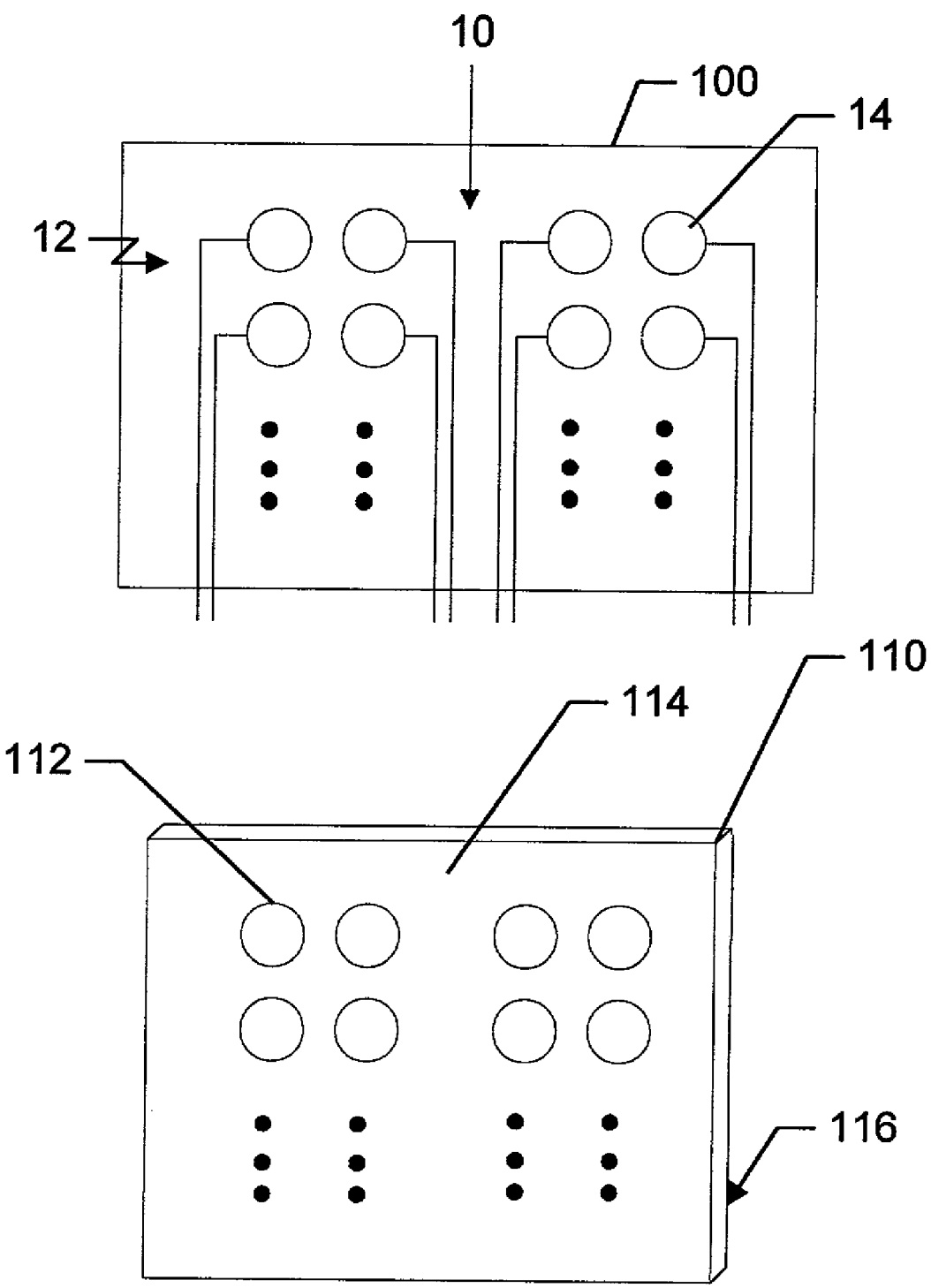
FIG. 2 illustrates an alternative system.

Referring now to FIG. 2 the matrix 10 and the connecting lines 16 may instead be housed in a pad 100. As appropriate, the pad 100 may also house the switching mechanism 30. The pad, and thus the matrix 10, attaches to a patient's back, preferably with a two-sided adhesive sheet 110. The sheet 110, with front and back sides 114 and 116, includes holes 112 that correspond to the locations of the electrodes 14, to allow the electrodes to be held directly in contact with the patient when the sheet 110 and pad 100 are in place. The sheet 110, which is made of medical grade adhesive, is preferably disposable, while the pad 100 and the included electrodes are re-usable. Alternatively, one or two sided adhesive strips may be used to hold the re-usable pad 100 in place.

Figure 3:
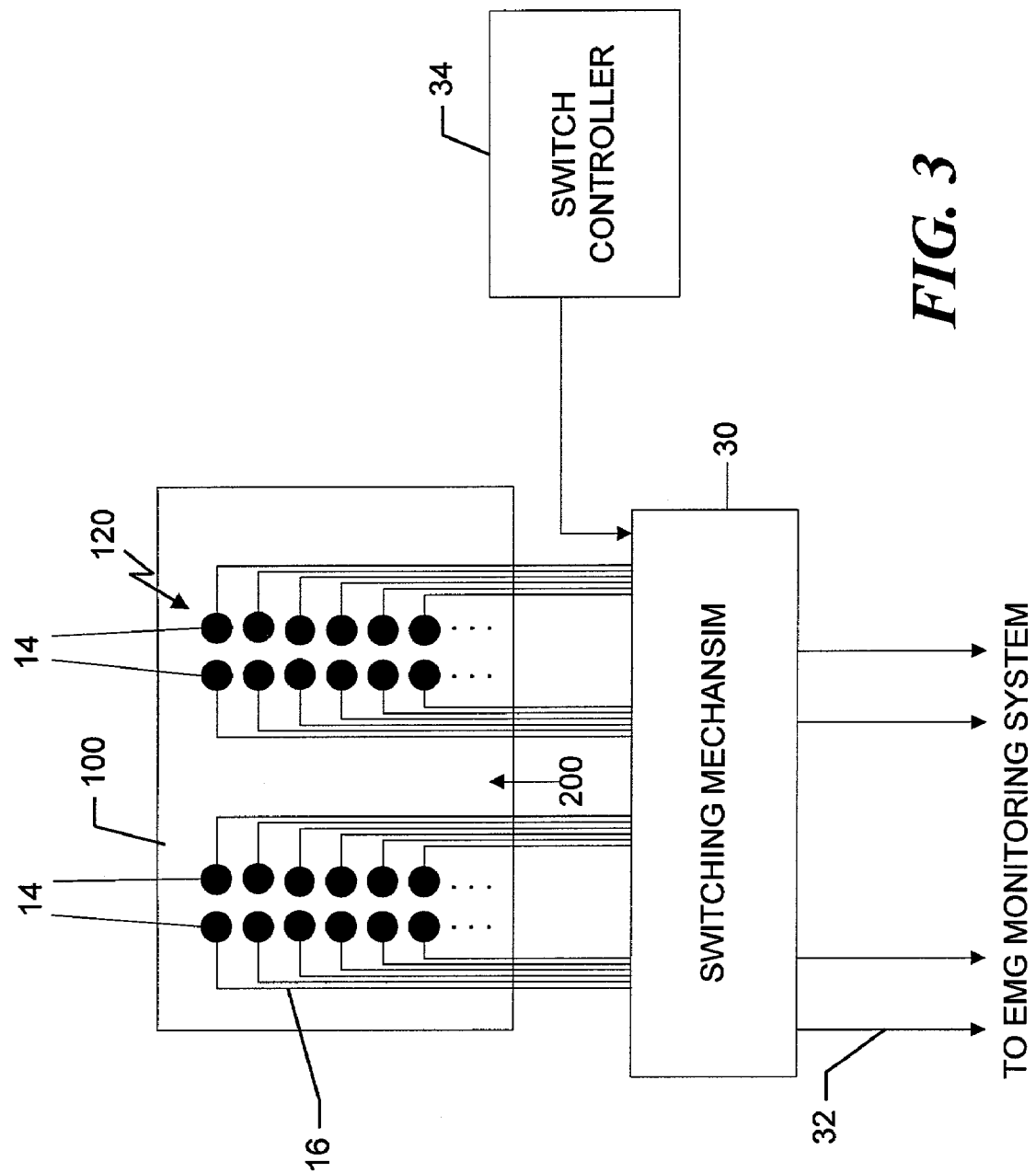
FIGS. 3 and 4 illustrate alternative embodiments of the systems of FIGS. 1 and 2.

Referring now to FIG. 3, an alternative matrix 200 is shown. The matrix 200 includes closely-spaced arrays 120 that may be used in different manners as described below for various sized patients. The switch controller 34, via the switching mechanism 30, passes the signals from adjacent arrays 120 for infant-sized patents, and selectively uses the signals from alternating arrays for relatively large patients. The switch controller 34 and the switching mechanism 30 may pass the signals from other arrangements of arrays, with various arrays skipped, and so forth, for even larger patients. As appropriate, the clinician enters data relating to the patient's size and/or directs the switching controller 34, to ensure that the appropriate arrays 120 are selected for the current protocol.

Figure 4:
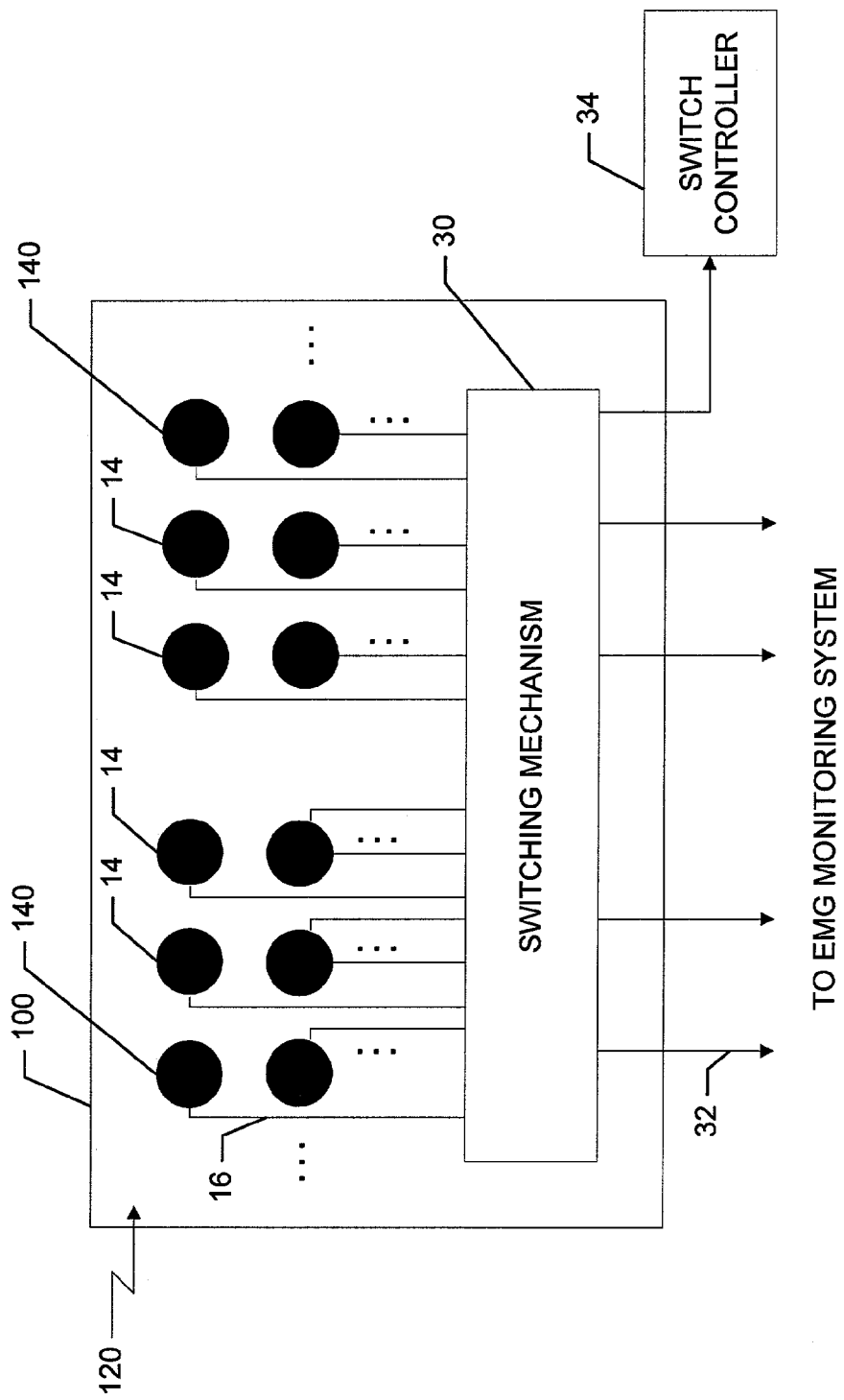

Further, as depicted in FIG. 4, redundant electrodes 140 may be included in the arrays 120. The electrodes 14 are spaced horizontally for relatively small patients and the redundant electrode is spaced from the inner-most electrode 14 to correspond to a relatively large patient. Each electrode connects electrically, via lines 16, to the switching mechanism, which selects sets of two electrodes per selected array. The clinician may thus enter data relating to the patient's size and/or direct the switch controller 34 to select different horizontal spacings for the different sized patients. For example, in the drawing, the two inner-most electrodes 14 in the selected arrays 120 are used for smaller patients while the two outer-most electrodes 14 and 140 may be used for larger patients. As appropriate, additional electrodes 140 may be included in the arrays 120, to accommodate various sized patients. The redundant electrodes 140 may also be included in the arrays 12 of respective sized matrices 10 (FIG. 1).

As discussed, the matrix may include electrodes that are spaced to correspond to specific sizes of patients, and various sizes of matrices may be used. Alternatively, one size matrix may be used, with the switching mechanism selecting specific electrodes for use based on the sizes of the respective patients. However, for a given patient, the matrix is held in a desired position relative to the spine, and required measurements can be taken in the various postures using the switching mechanism without having to re-position any of the electrode arrays.

As also discussed, redundant electrodes may be included in the various arrays, such that the switch controller not only selects particular arrays but also electrodes within the arrays. Further, the redundant electrodes may be included in every array or in particular arrays, as appropriate.

What is claimed is:

1. A system for routing electromyography signals to one or more electromyography amplifiers, the system including:
   A. a matrix for placement along a spine, the matrix including a plurality of electrodes arranged in sets of parallel arrays with the arrays arranged on either side of the spine when the matrix is in place along the spine the arrays being spaced vertically to correspond to the size of a relatively small patient;
   B. a switching mechanism that electrically connects selected electrode arrays to the amplifiers; and
   C. a switch controller that operates the switching mechanism to control the selection of the arrays, the switch controller directing the switching mechanism to connect to the amplifiers selected arrays that are spaced vertically to correspond to the size of the patient on which the matrix is arranged.

2. The system of claim 1 wherein the matrix is arranged in two adhesive strips that are placed on opposite sides of the spine when the system is in use.

3. The system of claim 1 wherein the matrix is housed in a re-usable pad.

4. The system of claim 3 further including a two-sided adhesive sheet that holds the pad in place along the spine when the system is in use.

5. The system of claim 4 wherein the adhesive sheet includes holes that correspond to the locations of the electrodes in the matrix.

6. The system of claim 3 wherein the pad further houses the switching mechanism.

7. A system for routing electromyography signals to one or more electromyography amplifiers, the system including:
   A. a matrix for placement along a spine, the matrix including a plurality of electrodes arranged in arrays with certain or all of the respective arrays further including one or more redundant electrodes that are spaced horizontally to correspond to various sizes of patients;
   B. a switching mechanism that electrically connects selected electrode arrays to the amplifiers; and
   C. a switch controller that operates the switching mechanism to control the selection of the arrays, the switch controller directing the switching mechanism to connect to the amplifiers, from selected respective arrays, selected electrodes and redundant electrodes that are spaced vertically to correspond to the size of the patient on which the matrix is arranged.

8. A system for routing electromyography signals to one or more electromyography amplifiers, the system including:
   A. a matrix for placement along a spine, the matrix including a plurality of electrodes arranged in arrays;
   B. a switching mechanism that electrically connects selected electrode arrays to the amplifiers; and
   C. a switch controller that operates the switching mechanism to control the selection of the arrays the switch controller being programmed to select arrays in accordance with various protocols and further programmed to select arrays in accordance with the size of the patient.

9. A system for routing electromyography signals to one or more electromyography amplifiers, the system including:
   A. a matrix for placement along a spine, the matrix including a plurality of electrodes arranged in parallel arrays;
   B. a switching mechanism that electrically connects selected arrays of the electrodes to the amplifiers;
   C. a pad for housing the matrix and lines that connect the electrodes and the switching mechanism;
   D. a switch controller that operates the switching mechanism to control the selection of the arrays, the switch controller being programmed to select arrays in accordance with various protocols and being further programmed to select arrays in accordance with the size of the patient.

10. The system of claim 9 wherein the pad further houses the switching mechanism.

11. The system of claim 9 wherein the switching mechanism simultaneously electrically connects two or more arrays to the amplifiers.

12. The system of claim 9 wherein the arrays arranged on either side of the spine when the matrix is in place along the spine.

* * * * *